United States Patent [19]

Kennedy

[11] Patent Number: 5,342,557
[45] Date of Patent: * Aug. 30, 1994

[54] PROCESS FOR PREPARING POLYMER PARTICLES

[75] Inventor: John Kennedy, Stratford, Conn.

[73] Assignee: United States Surgical Corporation, Norwalk, Conn.

[*] Notice: The portion of the term of this patent subsequent to Sep. 2, 2009 has been disclaimed.

[21] Appl. No.: 618,652

[22] Filed: Nov. 27, 1990

[51] Int. Cl.$^5$ .......................... B29B 9/00; B29B 9/02; B29B 9/10; B29B 9/12
[52] U.S. Cl. .......................................... 264/8; 264/13
[58] Field of Search .................. 264/8, 11, 14, 13; 425/8

[56] References Cited

U.S. PATENT DOCUMENTS

| | | | |
|---|---|---|---|
| 3,549,731 | 12/1970 | Kohn et al. | 264/8 |
| 3,741,703 | 6/1973 | Reynolds | 264/8 |
| 3,743,464 | 7/1973 | Strobert | 264/8 |
| 3,812,221 | 5/1974 | Smith et al. | 264/28 |
| 3,882,858 | 5/1975 | Klemm | 606/76 |
| 3,981,957 | 9/1976 | van Brederode et al. | 502/528 |
| 4,100,236 | 7/1978 | Gordon et al. | 264/8 |
| 4,113,440 | 10/1978 | Rinde | 264/28 |
| 4,165,420 | 8/1979 | Rinehart | 526/63 |
| 4,186,448 | 2/1980 | Brekke | 623/16 |
| 4,200,601 | 4/1980 | McClain | 264/9 |
| 4,256,677 | 3/1981 | Lee | 264/8 |
| 4,315,720 | 2/1982 | Ueda et al. | |
| 4,329,304 | 5/1982 | McClain | 264/8 |
| 4,336,210 | 6/1982 | McClain | 264/8 |
| 4,340,550 | 7/1982 | Ho | 264/13 |
| 4,430,451 | 2/1984 | Young et al. | 521/64 |
| 4,436,782 | 3/1984 | Ho | 428/402 |
| 4,485,055 | 11/1984 | Bung et al. | |
| 4,529,900 | 5/1985 | Castro | 264/41 |
| 4,535,485 | 8/1985 | Ashman et al. | 623/16 |
| 4,547,390 | 10/1985 | Ashman et al. | 523/114 |
| 4,578,502 | 3/1986 | Cudmore | 528/308.1 |
| 4,643,735 | 2/1987 | Hayes | 623/16 |
| 4,648,820 | 3/1987 | Scruggs et al. | |
| 4,663,447 | 5/1987 | Yamazaki et al. | 536/76 |
| 4,673,695 | 6/1987 | Aubert et al. | 521/64 |
| 4,675,140 | 6/1987 | Sparks et al. | 264/4.3 |
| 4,693,986 | 9/1987 | Vit et al. | 264/59 |
| 4,701,289 | 10/1987 | Liles et al. | |
| 4,734,227 | 3/1988 | Smith | 528/502 |
| 4,801,739 | 1/1989 | Franz et al. | 560/185 |
| 4,810,775 | 3/1989 | Bendix et al. | 528/480 |
| 4,822,534 | 4/1989 | Lencki et al. | 264/43 |
| 4,822,535 | 4/1989 | Ekman et al. | 264/4.3 |
| 4,835,139 | 5/1989 | Tice et al. | 514/15 |

(List continued on next page.)

FOREIGN PATENT DOCUMENTS

| | | |
|---|---|---|
| 0052793 | 6/1982 | European Pat. Off. |
| 265906 | 5/1988 | European Pat. Off. |
| 274898 | 7/1988 | European Pat. Off. |
| 0488218 | 6/1992 | European Pat. Off. |
| 661206 | 7/1987 | Switzerland |
| 2121203 | 12/1983 | United Kingdom |
| 2246571 | 2/1992 | United Kingdom |
| 9200342 | 1/1992 | World Int. Prop. O. |

OTHER PUBLICATIONS

Search Report from European Application No. 91120279 (26 Jun. 1992).
Search Report from European Appln. No. 92102262.0 (14 Sep. 1992).
NASA Tech Briefs, Sep. 1987, p. 50.
J. Microencapsulation, 1988; vol. 5, No. 2, 147–157.

*Primary Examiner*—John Kight, III
*Assistant Examiner*—Jeffrey Culpeper Mullis

[57] ABSTRACT

A process is provided for preparing particles of polymer by heating the polymer having an inherent viscosity not exceeding about 0.6 dl/g when measured at a temperature of about 30° C. in chloroform or hexafluoroisopropanol, dividing the heated polymer into particles, and then solidifying these particles such that substantially no fibers are formed among the particles.

27 Claims, 1 Drawing Sheet

U.S. PATENT DOCUMENTS

| | | | |
|---|---|---|---|
| 4,933,105 | 6/1990 | Fong | 264/12 |
| 4,933,182 | 6/1990 | Higashi et al. | 514/900 |
| 4,940,734 | 7/1990 | Ley et al. | 521/84.1 |
| 5,004,602 | 3/1991 | Hutchinson | 514/2 |
| 5,007,939 | 4/1991 | Delcommune et al. | |
| 5,015,423 | 5/1991 | Eguchi et al. | 264/9 |
| 5,015,667 | 5/1991 | Yoshimura et al. | 521/58 |
| 5,019,302 | 5/1991 | Sparks et al. | |
| 5,019,400 | 5/1991 | Gombotz et al. | 428/402.24 |
| 5,047,180 | 9/1991 | Steiner et al. | |
| 5,047,450 | 9/1991 | Wilder | 523/435 |
| 5,080,994 | 1/1992 | Breton et al. | 430/137 |
| 5,102,983 | 4/1992 | Kennedy | |
| 5,108,508 | 4/1992 | Rademachers et al. | 106/437 |
| 5,128,114 | 7/1992 | Schwartz | 423/335 |
| 5,143,662 | 9/1992 | Chesterfield et al. | 264/8 |
| 5,160,745 | 11/1992 | DeLuca et al. | 424/487 |

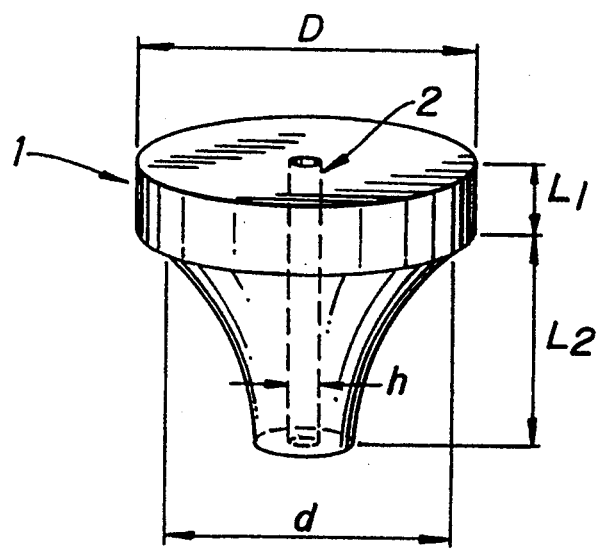
FIG_1
FIG_2
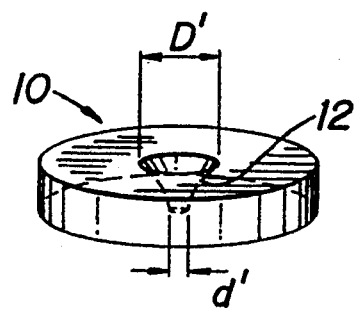

PROCESS FOR PREPARING POLYMER PARTICLES

BACKGROUND OF THE INVENTION

This invention relates to a process for preparing particles of polymer, e.g., spheroidal particulates or beads of the bioabsorbable variety, employing various individual atomization techniques such as melt extrusion and/or rotary atomization. The particles are useful, inter alia, in the repair of damaged or defective bone.

The medical use of polymer particles including those of the bioabsorbable variety are known, inter alia, from U.S. Pat. Nos. 3,882,858; 4,535,485; 4,547,390; 4,643,735; and 4,663,447. There has been an increase in interest in utilizing both bioabsorbable and non-absorbable particles to facilitate bone or fibrous tissue repair/reconstruction.

A number of processes are known for preparing finely divided polymeric particles, e.g., mechanical grinding, solvent precipitation, dispersion, and spray atomization of solutions or slurries. U.S. patent application Ser. No. 654,219, filed Feb. 12, 1991, now U.S. Pat. No. 5,143,662 describes producing particles of polymer by subjecting the polymer to rotary atomization. In rotary atomization, the polymer is applied to a rotation bell, cup or disk with mechanical forces predominating in the breakup of the polymer into particles. U.S. patent application Ser. No. 503,264, filed Apr. 2, 1990 and now U.S. Pat. No. 5,102,983 issued Apr. 7, 1992 describes a process for preparing foamed, bioabsorbable polymer particles by a freeze-drying technique.

Processes which form microspheres of absorbable material less than or equal to 0.2 mm in diameter for use in controlled release of drugs, are well-known. Such spheres have generally been formed by a solvent evaporation technique. Alternatively, polymeric microspheres, e.g., beads, of average particle size greater than or equal to 0.2 mm in diameter can be formed by an emulsion polymerization process. Such emulsion polymerization has been successfully utilized to form beads of polymethylmethacrylate and styrene.

For medical applications, it is often desirable to control not only the particle size distribution of the polymeric particles but level of fibers which are present as well.

SUMMARY OF THE INVENTION

The present invention is directed to a process for preparing particles from a polymer having fiber-forming properties comprising:

a) heating a polymer having an inherent viscosity not exceeding about 0.6 dl/g when measured at a temperature of about 30° C. in chloroform or hexafluoroisopropanol (HFIP);

b) dividing the thus-heated polymer into particles; and c) solidifying the polymer particles, such that substantially no fibers are formed among the solidified particles.

When the conditions of the present invention are followed, particles of polymer of substantially uniform size, e.g., microspheres of about 0.1 to about 3.0 mm average size (in diameter) can be prepared from polymeric substances, while fiber forming tendencies of the polymer are suppressed. In other words, the fiber forming tendency of the polymeric material, which is believed to relate to the surface tension exhibited by the polymer, is inhibited according to the present invention such that substantially no fibers are produced among the particles that are prepared. As used herein, the term "fiber" refers to materials which may be characterized as having a denier (see, e.g., *Plastics Terms Glossary, Fourth Edition*, Phillips Chemical Company, Bartlesville, Oklahoma).

The particles are preferably formed into spheres which can be used as a packing or molded part in dental or orthopedic applications in which a bony defect is filled with material. Such material then acts as a scaffold for new bony ingrowth while, in the case of bioabsorbable particles, being resorbed by the body, leaving behind a fully healed bone tissue structure.

BRIEF DESCRIPTION OF THE DRAWINGS

The present invention will be described in greater detail below, with reference to the accompanying drawings in which:

FIG. 1 is a perspective view of an extrusion die adapter which can be utilized in accordance with the present invention; and, FIG. 2 is a perspective view of another extrusion die adapter which can be utilized in accordance with the present invention.

DESCRIPTION OF THE PREFERRED EMBODIMENTS

In order to minimize the formation of fibers during the process of the present invention, a polymer is selected for processing which has an inherent viscosity not exceeding about 0.6 dl/g when measured at a temperature of about 30° C. in chloroform or HFIP (concentration of the polymer during this measurement is about 0.25 g/dl). HFIP is generally used as the measuring solvent when glycolide content exceeds about 40 mole percent of the overall polymer being measured. Preferably, the polymer has an inherent viscosity, when measured under these conditions, of about 0.2 to about 0.5 dl/g, more preferably about 0.25 to about 0 0.45 dl/g.

It should be noted that the polymer can have an initial inherent viscosity within the levels set forth above. Alternatively, the polymer can have an initial inherent viscosity exceeding about 0.6 dl/g when measured under the above conditions and then can be treated, e.g., heated, to cause degradation of the polymer, such as by hydrolysis (when heated in the presence of moisture), to reduce the viscosity to the levels set forth above. The polymer can then be further heated in accordance with the heating step of the present invention.

While not being bound by any particular theory on physical properties, it is believed that the polymer possessing an inherent viscosity not exceeding about 0.6 dl/g when measured under the above conditions, exhibits a reduced tendency to form fibers because of a physical attribute associated with the polymer, e.g., an increased surface tension and/or reduced chain lengths of individual polymer chains relative to higher inherent viscosity materials. The inherent viscosity is a function of, among other factors, the molecular weight of a polymer. Accordingly, the inherent viscosity of the polymer can be controlled by selecting a polymer having an appropriate molecular weight.

The polymer is preferably bioabsorbable and can be derived from polyglycolic acid, glycolide, lactic acid, lactide, dioxanone, e-caprolactone, trimethylene carbonate, etc., and various combinations of these and related monomers. Polymers of this type are known in the art, principally as materials for the fabrication of such surgical devices as sutures, wound clips, and the like, as disclosed, e.g., in U.S. Pat. Nos. 2,668,162; 2,703,316; 2,758,987; 3,225,766; 3,297,033; 3,422,181; 3,531,561; 3,565,077; 3,565,869; 3,620,218; 3,626,948; 3,636,956; 3,736,646; 3,772,420; 3,773,919; 3,792,010; 3,797,499; 3,839,297; 3,867,190; 3,878,284; 3,982,543; 4,047,533; 4,060,089; 4,137,921; 4,157,437; 4,234,775; 4,237,920; 4,300,565; and, 4,523,591; U.K. Patent No. 779,291; D. K. Gliding et al., "Biodegradable polymers for use in surgery - - polyglycolic/poly(lactic acid) homo- and co-polymers: 1", *Polymer*, Volume 20, pages 1459–1464 (1979), and D. F. Williams (ed.), *Biocompatibility of Clinical Implant Materials*, Vol. II, ch. 9: "Biodegradable Polymers" (1981). Copolymers of glycolide and lactide with or without additional monomers are preferred and of these glycolidelactide copolymers are most preferred.

The present invention may also be practiced on non-absorbable polymeric materials having fiber-forming properties such as nylon, polyester, polypropylene, polytetrafluoroethylene (PTFE), polyethylene terephthalate (Dacron), etc.

According to the present invention, the polymeric material is heated so as to produce a flowable mass. The polymer is preferably heated to a temperature from about 60° C. to about 300° C. More particularly, the temperature to which the polymeric material will be heated, will depend on the melt characteristics of the polymer selected. For example, for a glycolide/lactide copolymer, the system is heated to a temperature of from about 100° to about 300° C., preferably from about 170° C. to about 270° C., and most preferably from about 220° C. to about 250° C. For polymers having lower melting points, e.g., polycaprolactone, lower temperatures may be employed, e.g., about 60° C., whereas higher temperature may be required for materials having higher melting points.

After heating the polymer, the heated molten polymer is divided into particles with the molten particles then being solidified. The polymer is divided and solidified into the particles such that an average particle size (diameter) of the particles when solidified will be from about 0.1 to about 3 mm, more preferably from about 0.2 mm to about 1.5 mm, and most preferably from about 0.3 to about 1.0 mm.

In this regard, the molten polymer can be divided, e.g., into droplets, by being extruded through a capillary provided in an extrusion die of extrusion apparatus. Suitable extrusion apparatus which can be utilized in accordance with the present invention are described in G. A. Kruder, "Extrusion", *Encyclopedia of Polymer Science and Engineering* (Second Edition), Volume 6, pages 571–631, and in P. N. Richardson, "Plastics Processing", *Encyclopedia of Chemical Technology* (Third Edition), Volume 18, pages 185–189. Any part of the extrusion apparatus such as the extruder screw or the capillary die can be heated to the appropriate temperature in order to heat the polymer.

As the extrusion apparatus, an Instron Rheometer available from the Instron Corp. of Canton, Massachusetts 02021 can be used. The Instron Rheometer has an extrusion barrel of about 20 cm³ capacity and which is provided with a capillary die at the bottom thereof. The barrel is heated to the appropriate temperature and then loaded with the polymer, which is forced down through the capillary die by means of a plunger extending into the barrel.

Extrusion can be carried out through a capillary die adapter 1 illustrated in FIG. 1, having a capillary 2 of substantially constant inner diameter h. Alternatively, a capillary die adapter 20 of FIG. 2 can be utilized, which comprises a capillary 12 of narrowing inner diameter. Rate of extrusion and diameter size of the capillary determine ultimate particle size of solidified polymer particles. In particular, the capillary has a narrowest inner diameter of preferably about 0,010 to about 0.002 inch, more preferably about 0.009 to about 0.003 inch, and most preferably about 0.008 to about 0.004 inch. The polymer is extruded through the capillary preferably at a rate of about 15 to about 0.3 inch/min., more preferably at a rate of about 12 to about 0.5 inch/min., and most preferably at a rate of about 10 to about 1 inch/min.

Alternatively, the molten polymer can be divided into droplets, after being heated, by being sprayed through a spray nozzle. The spray nozzle itself can be heated to an appropriate temperature level in order to heat the polymer.

Furthermore the polymer can also be divided, after heating, by being applied onto a rotary atomizer upon whose surface the polymer breaks up into particles which are thrust away from the axis of the rotary atomizer. Suitable rotary atomizers which can be utilized in accordance with the present invention include those disclosed in U.S. Pat. Nos. 4,256,677; 3,741,703; and 3,743,464. A circular rotating element, e.g. a spinning disk of the rotary atomizer, can be flat, convex, concave, or even bell-shaped, and can contain protruding vanes on a surface thereof.

The size of the spinning disk itself and the rpm., i.e. rate of rotation, can be interrelated to provide the optimum centrifugal acceleration for the formation of the particles of bioabsorbable polymer. Variations of this centrifugal acceleration will affect the ultimate size of the particles that are formed. The revolutions of the spinning disk are controlled within a range of preferably about 100 to about 1000 rpm., more preferably within a range of about 130 to about 850 rpm., and most preferably within a range of about 160 to about 700 rpm. Furthermore, the disk itself is preferably between about 66 and about 86 cm. in diameter, more preferably between about 71 and about 81 cm. in diameter, and most preferably between about 75 and about 77 cm. in diameter. The instantaneous velocity of the disk is preferably controlled within a range of about 4 to about 40 m./sec., more preferably within a range of about 5 to about 35 m./sec., and most preferably within a range of about 6 to about 28 m./sec.

The bioabsorbable polymer is supplied in the form of a thin film onto a surface of the spinning disk of the rotary atomizer, whereby the centrifugal acceleration breaks the thin film into particles of the bioabsorbable polymer. Preferably, this film of polymer is applied about 0.01 to about 3.5 mm. thick on the spinning disk, more preferably about 0.1 to about 3.2 mm. thick, and most preferably of about 1.0 to about 3.0 mm. thick. Surface tension will cause the resulting particles of broken up polymer to ultimately harden into particles which are spheroidal or in the shape of beads, as these particles are radially discharged from the disk, i.e. fall off the edge of the rotary spinning disk of the rotary atomizer and are cooled. Varying the film thickness on the spinning disk or varying the feed rate of the flowable bioabsorbable polymer affects particle size, with the thinnest film causing the smallest particles to be formed.

Clearly, the molten polymer can be divided by other means within the context of the present invention. Once divided, the molten particles of polymer are solidified. Solidification can be carried out by allowing the extruded, sprayed or atomized particles to fall into a liquid which is immiscible with the molten polymer, which freezes the polymer particles on contact therewith, and in which the solidified polymer is not soluble. The freezing liquid can be, e.g., liquid nitrogen, and mixtures of solid carbon dioxide and a liquid such as acetone, pentane, etc. In general, the temperature of the freezing liquid is advantageously at least about 10° C. below the freezing temperature of the polymer particles. The lower the temperature of the freezing liquid, the faster the polymer particles will freeze solid therein. It is desirable to maintain a certain particle configuration, e.g., spheres upon freezing, and therefore rapid, even instantaneous freezing is called for. This can be conveniently achieved employing a freezing liquid such as liquid nitrogen.

The particles of frozen polymer can be recovered from the freezing liquid employing any suitable means, e.g., draining, straining, filtering, decanting or centrifuging, and the like. This operation is conducted at or below the melting point of the frozen polymeric particles to maintain the particles in the frozen state.

Alternatively, the polymeric particles can be solidified by falling freely through the air. The particles are allowed to fall a distance of at least about 40 cm. through the air, whereby the particles are sufficiently cooled before striking a collecting unit so that the particles will not stick together upon striking the collecting unit. More specifically, the particles are allowed to fall a distance of preferably about 190 to about 254 cm., more preferably about 200 to about 240 cm., and most preferably about 215 to about 230 cm. before striking the collecting unit. The collecting unit may be provided, e.g., as disclosed in U.S. Pat. Nos. 4,256,677 and 3,743,464.

The particles or beads formed of bioabsorbable or non-absorbable polymers can be used as filler in a surgical prosthesis, i.e. for implantation in a cavity provided in bone or fibrous tissue to encourage regrowth and regeneration of the tissue. The particles of the bioabsorbable polymer are absorbed by the body at a predictable rate allowing tissue or bony ingrowth as absorption takes place. The rate of absorption is characteristic of the polymer utilized. Thus, e.g., a glycolide-lactide copolymer will often completely resorb within six months in contrast to about two years for polyglycolide homopolymer. Both the bioabsorbable and nonabsorbable polymeric particles are readily molded to fill cavities or other contours. The beads can be heated to softening temperature, e g, to about 60° C., at which temperature they can be worked and shaped.

Any required drug, medicinal material, or growth factor can be incorporated into the polymer prior to processing, e.g. by addition to the polymer in the customary amounts so that at the conclusion of the polymeric particle manufacturing process herein, the particles will contain a predetermined amount of one or more of such substances.

Thus, it is within the scope of this invention to incorporate one or more medico-surgically useful substances into the particles, e.g., those which accelerate or beneficially modify the healing process when particles are applied to a surgical repair site. For example, the polymer particles can carry a therapeutic agent which will be deposited at the repair site. The therapeutic agent can be chosen for its antimicrobial properties, capability for promoting repair or reconstruction and/or new tissue growth or for specific indications such as thrombosis. Antimicrobial agents such as broad spectrum antibiotics (gentamicin sulphate, erythromycin or derivatized glycopeptides) which are slowly released into the tissue can be applied in this manner to aid in combating clinical and sub-clinical infections in a tissue repair site.

To promote repair and/or tissue growth, one or several growth promoting factors can be introduced into the particles, e.g., fibroblast growth factor, bone growth factor, epidermal growth factor, platelet derived growth factor, macrophage derived growth factor, alveolar derived growth factor, monocyte derived growth factor, magainin, and so forth. Some therapeutic indications are: glycerol with tissue or kidney plasminogen activator to cause thrombosis, superoxide dismutase to scavenge tissue damaging free radicals, tumor necrosis factor for cancer therapy or colony stimulating factor and interferon, interleukin-2 or other lymphokine to enhance the immune system.

The present invention will be explained in greater detail, by way of the following examples:

EXAMPLE 1

A capillary die adapter 1 of FIG. 1 having the following dimensions: D=0.730 inch; $L_1=\frac{1}{8}$ inch; $L_2=\frac{1}{8}$ inch; d=0.300 inch; and h=0.016 inch, was provided on a barrel of an Instron Rheometer extrusion apparatus. The extrusion apparatus, including the barrel and the adapter 1, was heated to 250° C. and then loaded with 25/75 mole percent glycolide/lactide copolymer having an inherent viscosity, measured at 30° C. in HFIP and at a concentration of 0.25 g/dl, of 0.49 dl/g. This copolymer was maintained in the barrel of the extrusion apparatus for 5 minutes and then extruded through capillary 2 of the die adapter 1 at a rate of 0.3 inch/min., whereby droplets of the polymer were formed. These droplets of the polymer were allowed to fall from the die adapter 1 a distance of 40 cm. and into a vat of liquid nitrogen at a temperature of −196° C., with the droplets of polymer thereby solidifying into beads. The beads were collected from the liquid nitrogen, classified, and were found to have an average diameter of 3 mm. The solidified polymer thus formed was substantially free of fibers.

This procedure was repeated, but with the 25/75 mole percent glycolide/lactide copolymer being exposed to air for 72 hours before being added to the heated extruder barrel. Clearer beads of a range of particle size of 2.8–3.1 mm were produced, the solidified polymer being substantially free of fibers.

EXAMPLE 2

The procedure of Example 1 was repeated, but with a die adapter disc 10 of FIG. 2 having a capillary 12 necking down from an inner entrance diameter D' of 1.25 mm to an inner exit diameter d' of 0.008 inch, with the extrusion apparatus including the adapter 10 being heated to a temperature of 225° C., and with respective rates of extrusion of 1 inch/min., 3 inch/min., and 10 inch/min. respectively for equal extruded amounts of the 25/75 mole percent glycolide/lactide copolymer having an inherent viscosity of 0.5 dl/g measured at 30° C. in HFIP and at a concentration of 0.25 g/dl. The extrudate formed a stream that broke into droplets upon exiting from the adapter 10, with the falling droplets being directed into a bucket of liquid nitrogen at −296° C. with stirring. A total of 15.65 g of beads (the product being substantially fiber free) was collected from these three combined runs and then classified, with the distribution being reported in Table II below:

TABLE II

| Sieve No.* | Weight (g) of Particles Retained Thereon | % of Particles Retained Thereon |
|---|---|---|
| 14 | 7.29 | 46.58 |
| 16 | 4.23 | 27.03 |
| 18 | 2.25 | 14.38 |
| 20 | 0.72 | 4.60 |
| 25 | 0.63 | 4.02 |
| 40 | 0.53 | 3.39 |
| Total | 15.65 g | Total 100.00% |

*a No. 14 sieve has openings of 1.41 mm;
a No. 16 sieve has openings of 1.19 mm;
a No. 18 sieve has openings of 1.00 mm;
a No. 20 sieve has openings of 0.841 mm;
a No. 25 sieve has openings of 0.707 mm; and
a No. 40 sieve has openings of 0.420 mm.

EXAMPLE 3

The procedure of Example 2 was repeated but with all molten polymer being extruded at a rate of 1 inch/min. A total of 6.96 g of beads was collected and then classified, with the distribution being reported in Table III below:

TABLE III

| Sieve No. | Weight (g) of Particles Retained Thereon | % Particles Retained Thereon |
|---|---|---|
| 14 | 0.84 | 12.07 |
| 16 | 1.71 | 24.57 |
| 18 | 1.99 | 28.59 |
| 20 | 1.83 | 26.29 |
| 25 | 0.25 | 3.59 |
| 40 | 0.30 | 4.31 |
| Passed Through 40 | 0.04 | 0.58 |
| Total | 6.96 g | Total 100.00% |

EXAMPLE 4

The procedure of Example 2 was repeated, but with all molten polymer being extruded at a rate of 3 inches/min. A total of 13.03 g of beads was collected and then classified, with the distribution being reported in Table IV below:

TABLE IV

| Sieve No. | Weight (g) of Particles Retained Thereon | % Particles Retained Thereon |
|---|---|---|
| 14 | 9.93 | 76.21 |
| 16 | 2.30 | 17.65 |
| 18 | 0.64 | 4.91 |
| 20 | 0.06 | 0.46 |
| 25 | 0.07 | 0.54 |
| 40 | 0.02 | 0.15 |
| Passed Through 40 | 0.01 | 0.08 |
| Total | 13.03 g | Total 100.00% |

EXAMPLE 5

The procedure of Example 2 was repeated, but with all molten polymer being extruded at a rate of 10 inches/min. A total of 19.62 g of beads was collected and then classified, with the distribution being reported in Table V below:

TABLE V

| Sieve No. | Weight (g) of Particles Retained Thereon | % Particles Retained Thereon |
|---|---|---|
| 14 | 13.49 | 68.76 |
| 16 | 3.38 | 17.23 |
| 18 | 1.35 | 6.88 |
| 20 | 0.63 | 3.21 |
| 25 | 0.38 | 1.94 |
| 40 | 0.32 | 1.63 |
| Passed Through 40 | 0.07 | 0.36 |
| Total | 19.62 g | Total 100.01%** |

**100.01% value due to rounding of significant figures.

EXAMPLE 6

The procedure of Example 3 was repeated in its entirety, but with the molten polymer being extruded through die adapter 10 having an extrusion channel 12 necking down from an entrance diameter D' of 1.25 mm to a minimum a diameter d' of 0.006 inch at the outlet thereof. A total of 5.94 g of beads was collected and then classified, with the distribution being reported in Table VI below:

TABLE VI

| Sieve No. | Weight (g) of Particles Retained Thereon | % Particles Retained Thereon |
|---|---|---|
| 14 | 0.70 | 11.78 |
| 16 | 1.09 | 18.35 |
| 18 | 1.45 | 24.41 |
| 20 | 1.17 | 19.70 |
| 25 | 0.88 | 14.82 |
| 40 | 0.58 | 9.76 |
| Passed Through 40 | 0.07 | 1.18 |
| Total | 5.94 g | Total 100.00% |

EXAMPLE 7

The procedure of Example 4 was repeated in its entirety, but with the molten polymer being extruded through die adapter 10 having an extrusion channel 12 necking down from an entrance diameter D' of 1.25 mm to a minimum diameter d' of 0.006 inch at the outlet thereof. A total of 8.49 g of beads was collected and then classified, with the distribution being reported in Table VII below:

TABLE VII

| Sieve No. | Weight (g) of Particles Retained Thereon | % Particles Retained Thereon |
|---|---|---|
| 14 | 2.58 | 30.39 |
| 16 | 2.89 | 34.04 |
| 18 | 2.15 | 25.32 |
| 20 | 0.39 | 4.59 |
| 25 | 0.23 | 2.71 |
| 40 | 0.18 | 2.12 |
| Passed Through 40 | 0.07 | 0.83 |
| Total | 8.49 g | Total 100.00% |

EXAMPLE 8

The procedure of Example 5 was repeated in its entirety, but with the molten polymer being extruded through a die adapter 10 having an extrusion channel 12 necking down from an entrance diameter D' of 1.25 mm to a minimum diameter d' of 0.006 inch at the outlet thereof. A total of 14.5 g of beads was collected and then classified, with the distribution being reported in Table VIII below:

TABLE VIII

| Sieve No. | Weight (g) of Particles Retained Thereon | % Particles Retained Thereon |
|---|---|---|
| 14 | 5.63 | 38.83 |
| 16 | 5.06 | 34.90 |
| 18 | 1.52 | 10.48 |
| 20 | 0.72 | 4.96 |
| 25 | 0.82 | 5.66 |
| 40 | 0.63 | 4.34 |
| Passed Through 40 | 0.12 | 0.83 |
| Total | 14.50 g | Total 100.00% |

EXAMPLE 9

The procedure of Example 2 was repeated in its entirety, but with the molten polymer additionally being stirred before extrusion. A total of 56.77 g of beads was collected and then classified, with the distribution being reported in Table IX below:

TABLE IX

| Sieve No. | Weight (g) of Particles Retained Thereon | % of Particles Retained Thereon |
|---|---|---|
| 14 | 22.36 | 39.39 |
| 16 | 17.00 | 29.95 |
| 18 | 11.78 | 20.75 |
| 20 | 1.99 | 3.51 |
| 25 | 1.66 | 2.92 |
| 40 | 1.62 | 2.85 |
| Passed Through 40 | 0.36 | 0.63 |
| Total | 56.77 g | Total 100.00% |

EXAMPLE 10

The procedure of Example 2 was repeated in its entirety, but with a die 10 having a channel 12 necking down from an entrance diameter D' of 1.25 mm to a minimum exit diameter d' of 0.006 inch. A total of 7.61 g of beads was collected and then classified, with the distribution being reported in Table X below:

TABLE X

| Sieve No. | Weight (g) of Particles Retained Thereon | % Particles Retained Thereon |
|---|---|---|
| 20 | 0.32 | 4.20 |
| 25 | 3.72 | 48.88 |
| 40 | 3.39 | 44.55 |
| Passed Through 40 | 0.18 | 2.37 |
| Total | 7.61 g | Total 100.00% |

EXAMPLE 11

The procedure of Example 7 was repeated in its entirety, but with polyglycolic acid (PGA), having an inherent viscosity of 0.25 dl/g measured at 30° C. in HFIP and at a concentration of 0.25 g/dl, being heated to 225° C. and then being extruded at a rate of 3 inch/min. A total of 10.04 g of PGA beads was collected and then classified, with the distribution being reported in Table XI below:

TABLE XI

| Sieve No. | Weight (g) of Particles Retained Thereon | % Particles Retained Thereon |
|---|---|---|
| 20 | 6.30 | 62.75 |
| 25 | 1.80 | 17.93 |
| 40 | 1.70 | 16.93 |
| Passed Through 40 | 0.24 | 2.39 |
| Total | 10.04 g | Total 100.00% |

EXAMPLE 12

The procedure of Example 11 was repeated, but with the polyglycolic acid (PGA) being heated to 240° C. and then being extruded (the PGA had an inherent viscosity of 0.25 dl/g at 30° C. in HFIP and at a concentration of 0.25 g/dl). A total of 5.52 g of PGA beads was collected and then classified, with the results being reported in Table XII below:

TABLE XII

| Sieve No. | Weight (g) of Particles Retained Thereon | % Particles Retained Thereon |
|---|---|---|
| 20 | 4.90 | 88.77 |
| 25 | 0.22 | 3.98 |
| 40 | 0.31 | 5.62 |
| Passed Through 40 | 0.09 | 1.63 |
| Total | 5.52 g | Total 100.00% |

What is claimed is:

1. Process for preparing particles of bioabsorbable polymer, comprising:
   a) heating to a temperature from about 60° to about 300° C., a polymer derived from monomers selected from the group consisting of glycolic acid, lactic acid, dioxanone, e-caprolactone and trimethylene carbonate and having an inherent viscosity between about 0.5 and about 0.6 dl/g when measured at a temperature of about 30° C. in chloroform or hexafluoroisopropanol, to form a molten or flowable mass;
   b) dividing the molten or flowable mass of thus-heated polymer into particles; and
   c) solidifying the thus-divided particles to form solidified polymer particles of average particle size of about 0.1 to about 3 mm;
   whereby substantially no fibers are formed among the solidified particles.

2. The process of claim 1, wherein the polymer has an initial inherent viscosity not exceeding about 0.6 dl/g when measured at the temperature of about 30° C. in chloroform or hexafluoroisopropanol.

3. The process of claim 1, wherein the polymer has an initial inherent viscosity above about 0.6 dl/g when measured at a temperature of about 30° C. in chloroform or hexafluoroisopropanol, and further comprising:
   treating the polymer so that the viscosity of the polymer is reduced to a level not exceeding about 0.6 dl/g when measured at 30° C. in chloroform or hexafluoroisopropanol and then heating the polymer in accordance with step (a).

4. The process of claim 3, wherein the polymer is treated by heating to cause the polymer to degrade.

5. The process of claim 4, wherein the polymer is heated in the presence of moisture to cause hydrolysis.

6. The process of claim 1, wherein the polymer is divided by extrusion through a capillary.

7. The process of claim 6, wherein the capillary has a minimum diameter from about 0.010 to about 0.002 inch.

8. The process of claim 7, wherein the minimum capillary diameter is from about 0.009 to about 0.003 inch.

9. The process of claim 8, wherein the minimum capillary diameter is from about 0.008 to about 0.004 inch.

10. The process of claim 6, wherein the polymer is extruded through the capillary at a rate of about 15 to about 0.3 inch/min.

11. The process of claim 10, wherein the extrusion rate is about 12 to about 0.5 inch/min.

12. The process of claim 11, wherein the extrusion rate is about 10 to about 1 inch/min.

13. The process of claim 1, wherein the polymer is divided by being sprayed through a nozzle.

14. The process of claim 1, wherein the polymer particles are solidified by being introduced into a liquid which is immiscible with the polymer and which freezes the polymer particles on contact therewith.

15. The process of claim 14, wherein the solidified polymer particles are insoluble in the liquid.

16. The process of claim 1, wherein the polymer particles are solidified by falling freely through air.

17. The process of claim 1, wherein the particles fall a distance of at least about 40 cm. through the air.

18. The process of claim 1, wherein the average particle size of the solidified particles is from about 0.2 to about 1.5 mm.

19. The process of claim 18, wherein the average particle size of the solidified particles is from about 0.3 to about 1.0 mm.

20. The process of claim 1, wherein the average particle size of the solidified particles is equal to or greater than about 0.42 mm.

21. The process of claim 1, wherein the polymer is heated to a temperature of from about 100° to about 300° C.

22. The process of claim 21, wherein the polymer is heated to a temperature of from about 170° to about 270° C.

23. The process of claim 22, wherein the polymer is heated to a temperature of from about 220° to about 250° C.

24. A process for preparing particles of bioabsorbable polymer, comprising:
a) heating to a temperature of from about 60° to about 300° C., a polymer derived from monomers selected from the group consisting of glycolic acid, lactic acid, dioxanone, e-caprolactone and trimethylene carbonate and having an inherent viscosity between about 0.5 and about 0.6 dl/g when measured at a temperature of about 30° C. in chloroform or hexafluoroisopropanol to form a molten or flowable mass;
b) dividing the molten or flowable mass of thus-heated polymer into particles, wherein the polymer is divided by being applied onto a rotary atomizer upon whose surface the molten polymer breaks up into particles which are thrust away from the axis of the rotary atomizer; and
c) solidifying the thus-divided particles to form solidified polymer particles of average particle size of about 0.1 to about 3 mm;
whereby substantially no fibers are formed among the solidified particles.

25. The process of claim 24, wherein the average particles size of the solidified particles is equal to or greater than about 0.42 mm.

26. A process for preparing particles of bioabsorbable polymer, comprising:
a) heating to a temperature from about 60° to about 300° C., a polymer derived from monomers selected from the group consisting of glycolic acid, lactic acid, dioxanone, e-caprolactone and trimethylene carbonate and having an inherent viscosity between about 0.2 and about 0.6 dl/g when measured at a temperature of about 30° C. in chloroform or hexafluoroisopropanol, to form a molten or flowable mass;
b) dividing the molten or flowable mass of thus-heated polymer into particles; and
c) solidifying the thus-divided particles by introducing the particles into a liquid which is immiscible with the polymer and which freezes the polymer particles on contact therewith, the liquid being selected from the group consisting of liquid nitrogen, and mixtures of solid carbon dioxide and a liquid, to form solidified polymer particles of average particle size of about 0.1 to about 3 mm;
whereby substantially no fibers are formed among the solidified particles.

27. Process for preparing particles of bioabsorbable polymer, consisting essentially of the steps of:
a) heating to a temperature from about 60° to about 300° C., a polymer derived from monomers selected from the group consisting of glycolic acid, lactic acid, dioxanone, e-caprolactone and trimethylene carbonate and having an inherent viscosity between about 0.5 and about 0.6 dl/g when measured at a temperature of about 30° C. in chloroform or hexafluoroisopropanol, to form a molten or flowable mass;
b) dividing the molten or flowable mass of thus-heated polymer into particles; and
c) solidifying the thus-divided particles to form solidified polymer particles of average particle size of about 0.42 to about 3 mm;
wherein substantially no fibers are formed among the solidified particles.

* * * * *